United States Patent [19]
Ritson

[11] Patent Number: 5,548,991
[45] Date of Patent: Aug. 27, 1996

[54] PERMEAMETER PROBE

[76] Inventor: Marc J. Ritson, 755 Weston Rd., Scotts Valley, Calif. 95066

[21] Appl. No.: 401,111

[22] Filed: Mar. 9, 1995

[51] Int. Cl.$^6$ .............................. G01M 3/26; G01N 3/00
[52] U.S. Cl. .............................. 73/38; 73/84; 73/864.74; 175/21
[58] Field of Search .............................. 73/38, 151, 155, 73/784, 864.43, 864.44, 864.45, 864.74, 864.81, 84, 85; 175/21, 50, 72, 65

[56] References Cited

U.S. PATENT DOCUMENTS

| 4,059,008 | 11/1977 | Torstensson | 73/38 |
| 4,148,212 | 4/1979 | Torstensson | 73/38 |
| 4,261,203 | 4/1981 | Snyder | 73/864.74 |
| 4,350,051 | 9/1882 | Thompson | 73/864.74 |
| 4,499,954 | 2/1985 | Diggle | 175/21 |

*Primary Examiner*—Michael J. Brock

[57] ABSTRACT

Relative permeability of subsurface earthen materials is measured by advancing a probe into the earthen material at a constant rate while simultaneously injecting a fluid sealant/lubricant, or vapor, or liquid, from the probe to the earthen material. The relative permeability of the earthen material is determined by measuring either changes in flow rate or pressure of the injected vapors or fluids. The prescribed method of operation of the probe seals the probe hole allowing collection of discrete vapor samples and also greatly facilitates advancement of the probe.

7 Claims, 1 Drawing Sheet

PERMEAMETER PROBE

SUMMARY OF THE INVENTION

The permeameter probe measures permeability of earthen material below ground surface by measuring continuously or incrementally the flow of fluid or vapor ejected from the permeameter probe as the probe penetrates subsurface earthen materials at a continuous rate.

BRIEF DESCRIPTION OF THE DRAWING

The sole FIGURE is a view of the permeameter probe of the invention.

DESCRIPTION OF THE PREFERRED EMBODIMENT

Figure 1:
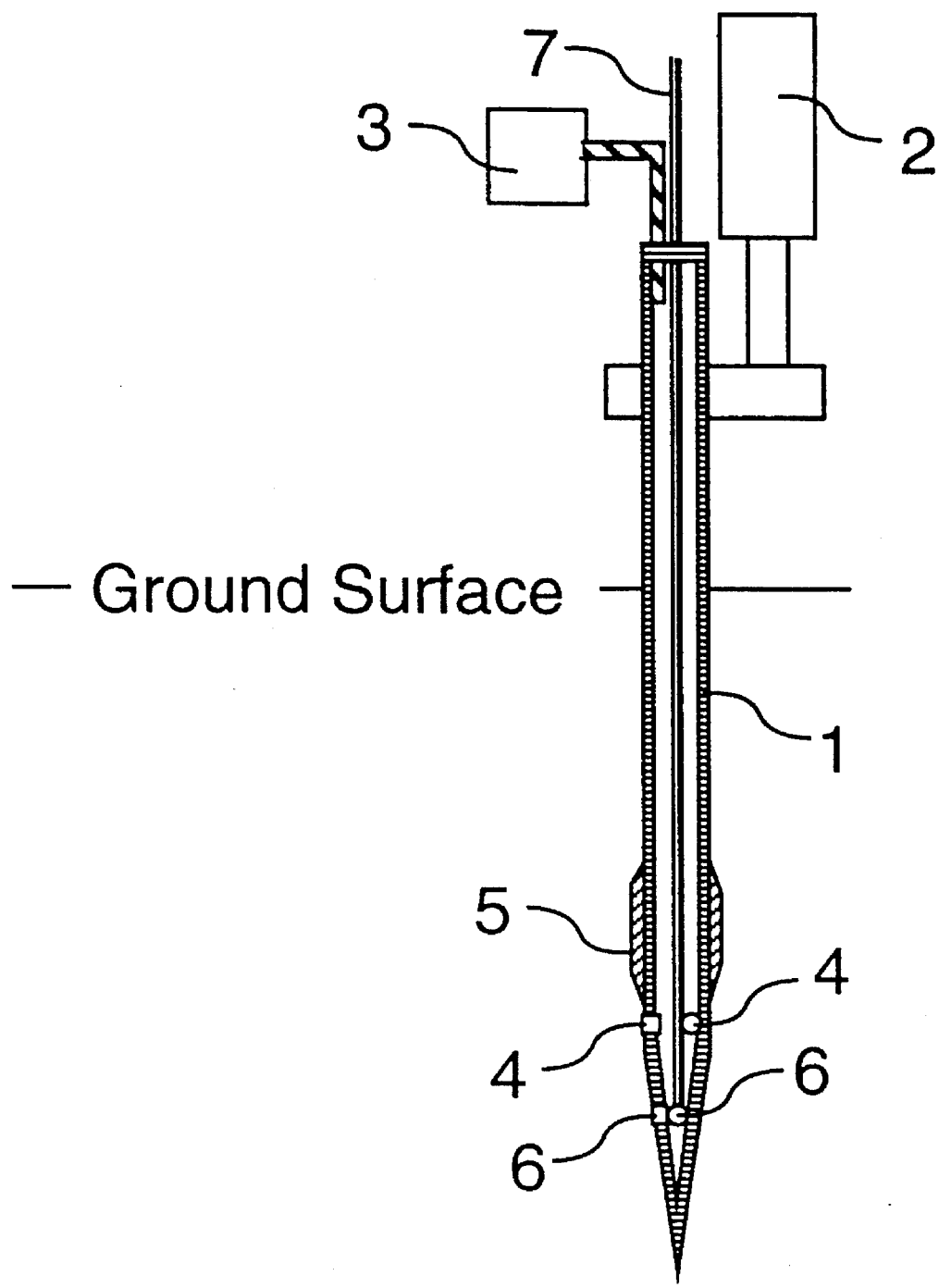

The probe (1) is pushed into the ground at a constant rate using a regulating device (2). Simultaneously a liquid lubricant/sealant is injected into the probe, under pressure at a constant flow rate or constant pressure (3). The liquid flows to the lubricant/sealant ports (4) and then to the adjacent earthen material. An expanded section of the probe (5) prevents the flow of lubricant/sealant upward through hole formed by advancing the probe. The change in pressure (for a constant flow rate system) or the change in flow rate (for a constant pressure system) of the lubricant/sealant is measured downstream of the flow or pressure control device, continuously or incrementally, and these changes are used to characterize the relative permeability of the earthen material continuously or incrementally.

A secondary permeability test port (6) can be included in the probe and is located below the lubricant/sealant ports. Gasses or liquids flow via an injection line (7) and are injected from the secondary port, ahead of the lubricant/sealant, into the earthen material. Relative permeability is measured in the same manner as described previously for injection of lubricant/sealant liquid.

Lubricant/sealant is used to fill the hole left by the probe at the time as the probe withdrawn from the sounding.

The pressure at which the probe is pushed can be measured and can be used to provide secondary characterization of the stiffness of the earthen material.

The permeameter probe characterizes continuously or incrementally the relative permeability of subsurface earthen material and fills and seals the hole left by the probe as the probe is withdrawn toward ground surface.

I claim:

1. A permeameter probe for measuring the relative permeability of earthen material below ground, comprising:

a hollow, tubular probe shaft with a hollow drive point at a first end;

drive means, at the second end of the probe shaft, for pushing the first end of the probe shaft into the ground at a constant rate;

means for injecting a liquid under pressure down the interior of the probe shaft, out of first ports in the drive point, and into the adjacent earthen material, as the probe shaft is a pushed into the ground;

an expanded section of the probe shaft above the drive point for preventing the injected liquid from flowing up the bore formed by the advancing probe shaft; and means for measuring a characteristic of the liquid injected into the adjacent earthen material and determining from said measurement the relative permeability of the adjacent earthen material.

2. The permeameter probe of claim 1 wherein the liquid is a lubricant.

3. The permeameter probe of claim 1 wherein the liquid is a sealant.

4. The permeameter probe of claim 1 wherein the means for injecting injects the liquid at a constant pressure, and the means for measuring measures the flow rate of the liquid as the characteristic of the liquid and determines the relative permeability from changes in the measured flow rate.

5. The permeameter probe of claim 1 wherein the means for injecting injects the liquid at a constant flow rate, and the means for measuring measures the pressure of the liquid as the characteristic of the liquid and determines the relative permeability from changes in the measured pressure.

6. The permeameter probe of claim 1 further comprising means for measuring the force with which the probe shaft is pushed into the ground, and means for characterizing the stiffness of the earthen material through which the probe is being pushed as a function of the measured force.

7. The permeameter probe of claim 1 further comprising:

a secondary test port located below the first ports;

an injection line in fluid communication with the secondary test port;

means for injecting a fluid through the injection line, out of the secondary test port and into adjacent earthen material below the liquid injected out of the first ports; and means for measuring a characteristic of the fluid injected out of the secondary test port to determine the relative permeability of the adjacent earthen material.

* * * * *